United States Patent
DeToffol

(10) Patent No.: US 7,755,477 B2
(45) Date of Patent: Jul. 13, 2010

(54) PORTABLE APPARATUS FOR PREVENTING DAMAGES FROM ELECTRO-MAGNETIC FIELD FOR IMPLANTABLE DEVICE IN HUMAN BODIES

(76) Inventor: Emil DeToffol, 809 Madison Ave., Albany, NY (US) 12208

(*) Notice: Subject to any disclaimer, the term of this patent is extended or adjusted under 35 U.S.C. 154(b) by 707 days.

(21) Appl. No.: 11/788,793

(22) Filed: Apr. 23, 2007

(65) Prior Publication Data
US 2007/0213779 A1 Sep. 13, 2007

Related U.S. Application Data

(63) Continuation-in-part of application No. 11/162,025, filed on Aug. 25, 2005, now abandoned.

(51) Int. Cl.
*G08B 1/08* (2006.01)
(52) U.S. Cl. ............... 340/539.12; 340/573.1; 340/539.11; 340/657

(58) Field of Classification Search ............ 340/573.1, 340/539.12, 539.1, 539.11, 657
See application file for complete search history.

(56) References Cited

U.S. PATENT DOCUMENTS

| | | | |
|---|---|---|---|
| 2004/0243193 A1* | 12/2004 | Ballis | 607/27 |
| 2009/0058635 A1* | 3/2009 | LaLonde et al. | 340/539.11 |
| 2009/0058636 A1* | 3/2009 | Gaskill et al. | 340/539.11 |
| 2009/0062887 A1* | 3/2009 | Mass et al. | 607/60 |
| 2009/0063193 A1* | 3/2009 | Barton et al. | 705/3 |

* cited by examiner

Primary Examiner—Travis R Hunnings

(57) ABSTRACT

An apparatus detects DC magnetic field, AC magnetic and electrical fields, and high frequency/microwave radiation, and alarms when the field strength is beyond the safety threshold. The threshold was set up based on pacemaker and other implantable device manufacturer's specifications and left enough safety margins to give early warning before the sources actually start interfering with the implanted devices.

1 Claim, 1 Drawing Sheet

PORTABLE APPARATUS FOR PREVENTING DAMAGES FROM ELECTRO-MAGNETIC FIELD FOR IMPLANTABLE DEVICE IN HUMAN BODIES

This is a continuation-in-part application of the U.S. Ser. No. 11/162,025 filed on Aug. 25, 2005 now abandoned, entitled Pace-alert.

REFERENCE CITED

U.S. Pat. No. 5,647,379. July 1997
Other publications
http://lessemf.com/combi.html
http://osuntech.com/radiation.html

FILED OF THE INVENTION

This invention relates to the Electric and Magnetic Field (EMF) detection, measurement, and alert for implantable device users. This portable apparatus has special functions and works in wide frequency ranges that make the invention unique and novel.

BACKGROUND OF THE INVENTION

To implantable device users the EMF may cause life-threatening effects. When pacemakers are installed, most doctors warn patients to stay away from EMF, and Radio Frequency (RF) sources. However, EMF and RF are invisible and today's life is full of electrical appliances. How to know when to avoid electrical interference is a bothersome matter for the pacemaker and other implantable device patients. Our apparatus addresses this issue.

Although those implantable devices have adopted some improvements to reduce the sensitivity from EMF and RF, there are still substantial amount of reported cases where patients were affected by the electrical/magnetic sources. There are also some complementary implantable devices intended to detect the EMF for the implantable devices. For example, Meltzer (U.S. Pat. No. 5,647,379) discloses such a device in 1997. It can be implanted near the pacemakers or defibrillators to detect pulsed interferences. However there are other sources which could cause damage to the pacemakers or defibrillators, and there is a need to cover a wider frequency range for today's modern electrical equipment. In addition to that, this portable detector has no surgery involved so it is less complicated and the price is much lower. Patients can use it to discover which equipment has the potential to harm their implanted devices and maybe make some alterations to make the environment safer for them. For example, they can use the apparatus to discover which brand of equipment is safe for them and which is not, then they can switch to the safe one. They can also get to know what is the distance they should stay away from some equipment. They can use it whenever they need it and put is aside after they are familiar with the environment and have confidence that the electrical equipment will not affect their implantable devices. There are many patents and publication about implantable devise such as pacemakers or defibrillators. One example is Krause et al. (U.S. Pat. No. 6,434,429 B1). However there are few of patents and publications contributing to the protection of the implantable devices.

One related issue is that EMF has different properties and different ways of causing harmful biological effects. Some people become ill from many types of EMF sources, such as alarm clocks too close to their bed, sitting too close to a TV or computer, or using a cell phone. Reported symptoms are headaches, arm and leg tingling, dizziness, difficulty in concentrating, and even nausea. Although not proven, more serious problems might be caused by prolonged exposure to EMF. Most scientists agree that it is wise to protect ourselves from biological effects that are known to exist. For this purpose there are some EMF detectors on the market, e.g. Tri-Field meter, and Radiation Finder. However, the thresholds and frequency ranges of normal EMF detectors and our apparatus are different and therefore the circuits to realize the detection are different accordingly. In addition to that our apparatus in the invention covers all the sources that could cause damage to the implantable devise which TriField meter, and Radiation Finder do not.

Strong EMF Sources that could interfere the implanted devices:

Strong EMF sources in our environment highly depend on what people do, where people go, and how people live. For example, if people live in downtown of a big city they may encounter many sources; if they are an electrician or welder then they definitely get close to electrical equipment more than other people. There are some common sources they could use to test the unit from time to time:

1. On the door seal of microwave ovens.
2. Less than 1 inch from the AC/DC adaptor used for the answering machine, CD player, or other small appliances.

SUMMARY OF THE INVENTION

The present general invention concept provides a sensor, a signal processing system, and a display set specially for each of the channels at the threshold suitable for the implantable devices and wide frequency ranges covering today's mostly often used electrical equipment.

DETAILED DESCRIPTION OF THE PREFERRED EMBODIMENTS

Figure 1:
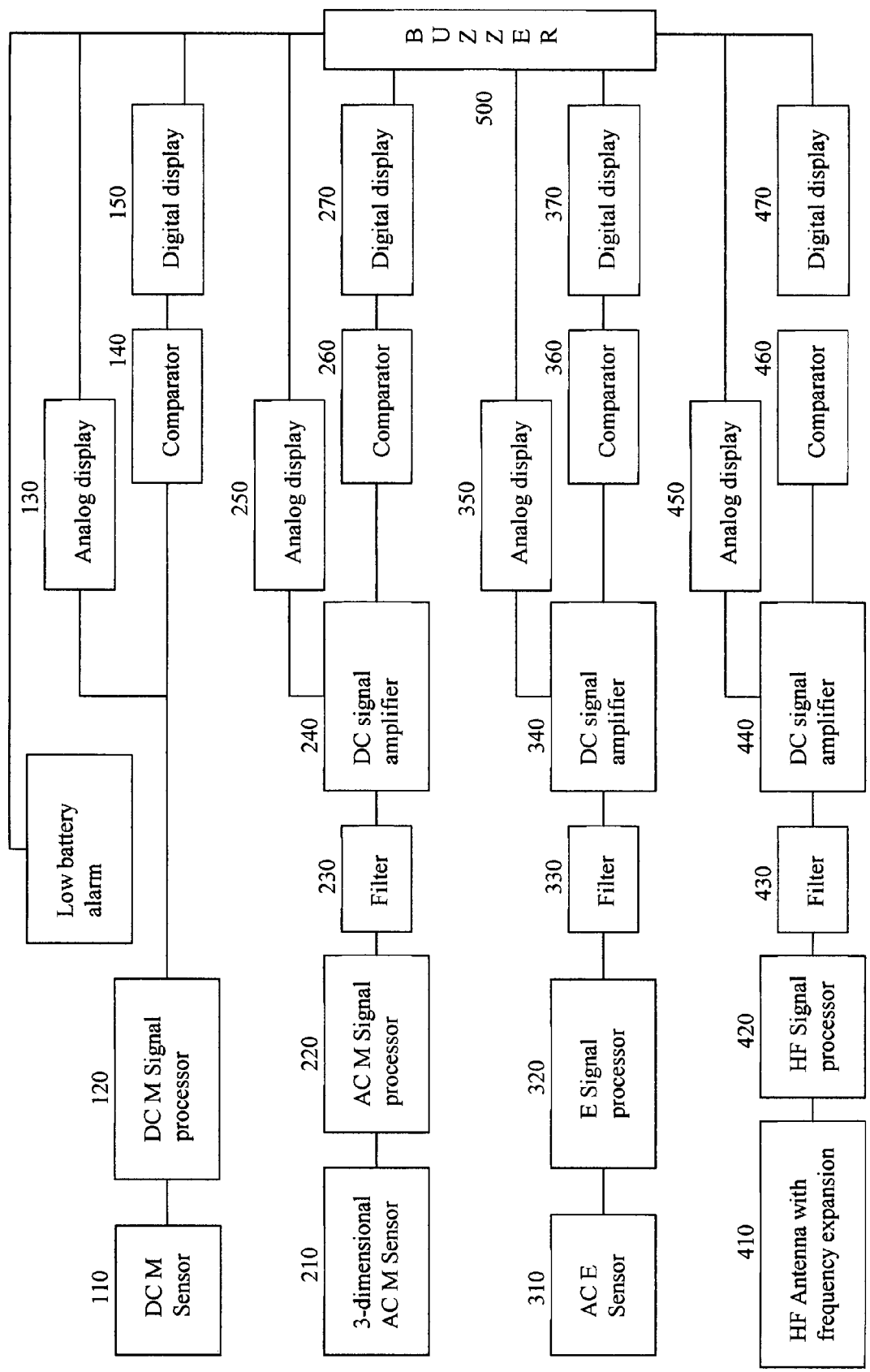
FIG. 1 is a block schematic diagram of the apparatus for detecting EMF/RF for implantable medical devices.

The invention provides an apparatus for detecting dangerous intensities of EMF that could interfere with or affect the operation of implantable medical devices, such as a cardiac pacemaker or defibrillator.

In FIG. 1, there are four channels for DC magnetic field, AC magnetic field, electrical field, and RF/microwave radiation individually.

For the DC magnetic field, Hall-effect sensor 110 picks up a voltage level when a strong DC magnetic field exists. Then it is coupled to a signal processor 120 to remove noise, and other unwanted components. The output signal then can be displayed directly with an analog meter or LED 130. The signal can also be sent to a comparator 140 to produce a digital output. The circuit starts picking up the signal at 0.5 Gauss, and the threshold of the comparator is set to 6 Gauss. Once the voltage level exceeds 6 Gauss, then the digital display unit 150 becomes active and sets alarm off and a LED is lit to show the danger. The threshold of the comparator can be adjusted to other updated numbers set by the implantable device manufacturers.

For the AC magnetic field, inductive pick-up devices may be provided to detect magnetic interference. The sensor 210 picks up a signal when a strong AC magnetic field exists. This sensor is a tri-axial, or consists of three sensors arranged at X, Y, and Z positions respectively. Then the signal is coupled to a signal processor 220 to remove noise, and other unwanted components based on the characteristics of this signal. The output signal is then sent to a filter 230 to obtain the DC level of the signal. After that there is another DC amplifier stage 240 for making the signal strong enough for the analog meter or LED 250, or the comparator 260. The circuit picks up the signal starting from 0.1 mG. Once the voltage level exceeds 1.5 Gauss, then the digital display unit 270 becomes active and sets alarm off and a LED is lit to show the danger. For this channel, frequency range is 30 Hz to 5 KHz, calibrated at 60 Hz. The threshold of the comparator can be adjusted to other updated numbers set by the implantable device manufacturers.

For the AC electrical field, the plate-shape sensor 310 picks up a signal when a strong AC electrical field exists. Then it is coupled to a signal processor 320 to remove noise, and other unwanted components based on the characteristics of this signal. The output signal is then sent to a filter 330 to obtain the DC level of the signal. After that there is another DC amplifier stage 340 for making the signal strong enough for the analog meter or LED 350 or comparator 360. The circuit picks up the signal starting from 1 KV/m. Once the voltage level exceeds 4 KV/m or other numbers set by the implantable device manufacturers at the comparator, then the digital display unit 370 becomes active and sets alarm off and a LED is lit to show the danger. For this channel, frequency range is from 30 Hz to 5 KHz, calibrated at 60 Hz.

For the RF/microwave field, the on-board antenna 410 picks up a signal when a strong RF/microwave radiation exists. This stage also includes a capacitor-coupled frequency expansion circuit to reach up to 5.5 GHz for the frequency range. Then the signal is coupled to a signal processor 420 to remove noise, and other unwanted components based on the characteristics of this signal. The output signal is then sent to a filter 430 to obtain the DC level of the signal. After that there is another DC amplifier stage 440 for making the signal strong enough for the analog meter or LED 450 or comparator 460. The circuit picks up the signal starting from 0.2 mW/cm$^2$. Once the voltage level exceeds 2.65 mW/cm$^2$ or other numbers set by the implantable device manufacturers at the comparator, then the digital display unit 470 becomes active and sets alarm off and a LED is lit to show the danger. For this channel, frequency range is from 500 KHz to 6 GHz, calibrated at 2.45 GHz.

All the channels are coupled to a buzzer to provide an audible alarm signal in addition to the visual or mechanical alarm signals. As long as one channel become active, the buzzer would go off.

What is claimed is:

1. A portable apparatus for preventing damages from DC magnetic field, AC magnetic and electrical fields, and high frequency/microwave radiation for implantable devices comprising:
   a channel for detecting DC magnetic field from 0.5 Gauss to 10 Gauss, and alarms when the field exceeds a threshold set by the implantable device manufacturers;
   a channel for detecting AC magnetic field from 1 mGauss to 3 Gauss, and alarms when the field exceeds a threshold set by the implantable device manufacturers;
   a channel for detecting AC electrical field from 1 KV/m to 8 KV/m, and alarms when the field exceeds a threshold set by the implantable device manufacturers;
   a channel for detecting RF/microwave radiation from 0.2 mW/cm$^2$ to 5 mW/cm$^2$, and alarms when the field exceeds a threshold set by the implantable device manufacturers; and
   a low battery alarm circuit; and
   wherein the DC magnetic field detection channel further comprising:
      a DC magnetic field sensor;
      a DC signal processor;
      a comparator; and
      an analog display unit comprising a meter, or bar LED display, or vibrator, or flashing light, to provide visual and mechanical alarm signal for this application, or a digital display unit comprising individual LEDs or bar LED display to provide visual alarm signal;
   wherein the AC magnetic field detection channel further comprising:
      an AC magnetic field sensor;
      an AC signal processor;
      a comparator; and
      an analog display unit comprising a meter, or bar LED display, or vibrator, or flashing light, to provide visual and mechanical alarm signal for this application, or a digital display unit comprising individual LEDs or bar LED display to provide visual alarm signal;
   wherein the AC electrical field detection channel further comprising:
      an AC electrical field sensor;
      an AC signal processor;
      a comparator; and
      an analog display unit comprising a meter, or bar LED display, or vibrator, or flashing light, to provide visual and mechanical alarm signal for this application, or a digital display unit comprising individual LEDs or bar LED display to provide visual alarm signal;
   wherein the RF/microwave radiation detection channel further comprising:
      a RF/microwave radiation sensor;
      a RF/microwave signal processor;
      a comparator, and
      an analog display unit comprising a meter, or bar LED display, or vibrator, or flashing light, to provide visual and mechanical alarm signal for this application, or a digital display unit comprising individual LEDs or bar LED display to provide visual alarm signal; and
   the display unit, either analog or digital, further connected to a buzzer to provide audible alarm signal.

* * * * *